United States Patent [19]

Antos

[11] 4,292,207

[45] Sep. 29, 1981

[54] NONACIDIC SUPERACTIVE MULTIMETALLIC CATALYTIC COMPOSITE FOR USE IN HYDROCARBON DEHYDROGENATION

[75] Inventor: George J. Antos, Bartlett, Ill.

[73] Assignee: UOP Inc., Des Plaines, Ill.

[21] Appl. No.: 133,232

[22] Filed: Mar. 24, 1980

Related U.S. Application Data

[60] Division of Ser. No. 34,810, Apr. 30, 1979, Pat. No. 4,210,769, which is a continuation-in-part of Ser. No. 907,240, May 18, 1978, Pat. No. 4,157,989, which is a division of Ser. No. 833,332, Sep. 14, 1977, Pat. No. 4,165,276.

[51] Int. Cl.$^3$ .......................... B01J 21/04; B01J 23/58
[52] U.S. Cl. .............................. 252/466 PT; 252/443; 252/473; 252/474; 585/434; 585/444; 585/660
[58] Field of Search ................. 252/443, 466 PT, 473, 252/474; 585/434, 444, 660

[56] References Cited

U.S. PATENT DOCUMENTS

3,535,402  10/1970  Kluksdahl .................. 252/466 PT
3,903,191  9/1975   Pollitzer .......................... 585/660

Primary Examiner—W. J. Shine
Attorney, Agent, or Firm—James R. Hoatson, Jr.; Louis A. Morris; William H. Page, II

[57] ABSTRACT

Dehydrogenatable hydrocarbons are dehydrogenated by contacting them, at hydrocarbon dehydrogenation conditions, with a novel nonacidic superactive multimetallic catalytic composite comprising a combination of a catalytically effective amount of a pyrolyzed rhenium carbonyl component with a porous carrier material containing a uniform dispersion of catalytically effective amounts of an alkali or alkaline earth component and of a platinum group component which is maintained in the elemental metallic state during the incorporation of the rhenium carbonyl component.

12 Claims, No Drawings

NONACIDIC SUPERACTIVE MULTIMETALLIC CATALYTIC COMPOSITE FOR USE IN HYDROCARBON DEHYDROGENATION

CROSS-REFERENCE TO RELATED APPLICATIONS

This application is a division of my prior, copending application Ser. No. 34,810 filed Apr. 30, 1979 now U.S. Pat. No. 4,210,769, issued on July 1, 1980; which in turn is a continuation-in-part of my prior application Ser. No. 907,240 filed May 18, 1978, and issued on June 12, 1979 as U.S. Pat. No. 4,157,989; which in turn is a division of my prior application Ser. No. 833,332 filed Sept. 14, 1977, and issued on Aug. 21, 1979 as U.S. Pat. No. 4,165,276. All of the teachings of these prior applications are specifically incorporated herein by reference.

The subject of the present invention is, broadly, an improved method for dehydrogenating a dehydrogenatable hydrocarbon to produce a hydrocarbon product containing the same number of carbon atoms but fewer hydrogen atoms. In another aspect, the present invention involves a method of dehydrogenating normal paraffin hydrocarbons containing 3 to 30 carbon atoms per molecule to the corresponding normal mono-olefin with minimum production of side products. In yet another aspect, the present invention relates to a novel superactive nonacidic multimetallic catalytic composite comprising a combination of a catalytically effective amount of a pyrolyzed rhenium carbonyl component with a porous carrier material containing a uniform dispersion of catalytically effective amounts of an alkali or alkaline earth component and a platinum group component which is maintained in the elemental state. This nonacidic composite has highly beneficial characteristics of activity, selectivity, and stability when it is employed in the dehydrogenation of dehydrogenatable hydrocarbons such as aliphatic hydrocarbons, naphthene hydrocarbons, and alkylaromatic hydrocarbons.

The conception of the present invention followed from my search for a novel catalytic composite possessing a hydrogenation-dehydrogenation function, a controllable cracking function, and superior conversion, selectivity, and stability characteristics when employed in hydrocarbon conversion processes that have traditionally utilized dual-function catalytic composites. In my prior application Ser. No. 833,332, I disclosed a significant finding with respect to a multimetallic catalytic composite meeting these requirements. More specifically, I determined that a pyrolyzed rhenium carbonyl component can be utilized, under certain specified conditions, to beneficially interact with the platinum group component of a dual-function catalyst with a resulting marked improvement in the performance of such a catalyst. Now I have ascertained that a catalytic composite, comprising a combination of catalytically effective amounts of a platinum group component and of a pyrolyzed rhenium carbonyl component with a porous carrier material can have superior activity, selectivity and stability characteristics when it is employed in a hydrocarbon dehydrogenation process if these components are uniformly dispersed in the porous carrier material in the amounts specified hereinafter and if the oxidation state of the platinum group component is carefully controlled so that substantially all of this component is present in the elemental metallic state during the incorporation of the rhenium carbonyl component. I have discerned, moreover, that a particularly preferred multimetallic catalytic composite of this type contains not only a platinum group component, and a pyrolyzed rhenium carbonyl component, but also an alkali or alkaline earth component in an amount sufficient to ensure that the resulting catalyst is nonacidic.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasolines, perfumes, drying oils, ion-exchange resins, and various other products well known to those skilled in the art. One example of this demand is in the manufacture of high octane gasoline by using $C_3$ and $C_4$ mono-olefins to alkylate isobutane. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of a vast number of other chemical products. For example, derivatives of normal mono-olefins have become of substantial importance to the detergent industry where they are utilized to alkylate an aromatic, such as benzene, with subsequent transformation of the product arylalkane into a wide variety of biodegradable detergents such as the alkylaryl sulfonate types of detergents which are more widely used today for household, industrial, and commercial purposes. Still another large class of detergents produced from these normal mono-olefins are the oxyalkylated phenol derivatives in which the alkylphenol base is prepared by the alkylation of phenol with these normal mono-olefins. Still another type of detergent produced from these normal mono-olefins are the biodegradable alkylsulfonates formed by the direct sulfation of the normal mono-olefins. Likewise, the olefin can be subjected to direct sulfonation with sodium bisulfite to make biodegradable alkylsulfonates. As a further example, these mono-olefins can be hydrated to produce alcohols which then, in turn, can be used to produce plasticizers and/or synthetic lube oils.

Regarding the use of products made by the dehydrogenation of alkylaromatic hydrocarbons, they find wide application in the petroleum, petrochemical, pharmaceutical, detergent, plastic, and the like industries. For example, ethylbenzene is dehydrogenated to produce styrene which is utilized in the manufacture of polystyrene plastics, styrene-butadiene rubber, and the like products. Isopropylbenzene is dehydrogenated to form alpha-methylstyrene which, in turn, is extensively used in polymer formation and in the manufacture of drying oils, ion-exchange resins, and the like materials.

Responsive to this demand for these dehydrogenation products, the art has developed a number of alternative methods to produce them in commercial quantities. One method that is widely utilized involves the selective dehydrogenation of a dehydrogenatable hydrocarbon by contacting the hydrocarbon with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here, these terms are generally defined for a given reactant as follows: (1) activity is a measure of the catalyst's ability to convert the hydrocarbon reactant into products at a specified severity level where severity level means the specific reaction conditions used—that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters—obviously, the smaller rate implying the more stable catalyst. In a dehydrogenation process, more specifically, activity commonly refers to the amount of conversion that takes place for a given dehydrogenatable hydrocarbon at a specified severity level and is typically measured on the basis of disappearance of the dehydrogenatable hydrocarbon; selectivity is typically measured by the amount, calculated on a mole or weight percent of converted dehydrogenatable hydrocarbon basis, of the desired dehydrogenated hydrocarbon obtained at the particular activity or severity level; and stability is typically equated to the rate of change with time of activity as measured by disappearance of the dehydrogenatable hydrocarbon and of selectivity as measured by the amount of desired dehydrogenated hydrocarbon produced. Accordingly, the major problem facing workers in the hydrocarbon dehydrogenation art is the development of a more active and selective catalytic composite that has good stability characteristics.

I have now found a superactive multimetallic catalytic composite which possesses improved activity, selectivity, and stability when it is employed in a process for the dehydrogenation of dehydrogentable hydrocarbons. In particular, I have determined that the use of a superactive multimetallic catalyst, comprising a combination of catalytically effective amounts of a platinum group component and a pyrolyzed rhenium carbonyl component with a porous refractory carrier material, can enable the performance of a hydrocarbon dehydrogenation process to be substantially improved if the platinum group component is uniformly dispersed throughout the carrier material prior to incorporation of the rhenium carbonyl component, if the oxidation state of the platinum group component is maintained in the elemental metallic state prior to and during contact with the rhenium carbonyl component and if high temperature treatments in the presence of oxygen and/or water of the reaction product of the rhenium carbonyl with the carrier material containing the platinum group component is avoided. Moreover, particularly good results are obtained when this composite is combined with an amount of an alkali or alkaline earth component sufficient to ensure that the resulting catalyst is nonacidic and utilized to produce dehydrogenated hydrocarbons containing the same carbon structure as the reactant hydrocarbon but fewer hydrogen atoms. This nonacidic composite is particularly useful in the dehydrogenation of long chain normal paraffins to produce the corresponding normal mono-olefin with minimization of side reactions such as skeletal isomerization, aromatization, cracking and polyolefin formation. In sum, the present invention involves the significant finding that a pyrolyzed rhenium carbonyl component can be utilized under the circumstances specified herein to beneficially interact with and promote a hydrocarbon dehydrogenation catalyst containing a platinum group metal.

It is, accordingly, one object of the present invention to provide a novel method for the dehydrogenation of dehydrogenatable hydrocarbons utilizing a superactive multimetallic catalytic composite comprising catalytically effective amounts of a platinum group component, and a pyrolyzed rhenium carbonyl component combined with a porous carrier material. A second object is to provide a novel nonacidic catalytic composite having superior performance characteristics when utilized in a hydrocarbon dehydrogenation process. Another object is to provide an improved method for the dehydrogenation of normal paraffin hydrocarbons to produce normal mono-olefins which method minimizes undesirable side reactions such as cracking, skeletal isomerization, polyolefin formation, disproportionation and aromatization.

In brief summary, one embodiment of the present invention involves a method for dehydrogenating a dehydrogenatable hydrocarbon which comprises contacting the hydrocarbon at hydrocarbon dehydrogenation conditions with a superactive multimetallic catalytic composite comprising a porous carrier material containing a uniform dispersion of catalytically effective and available amounts of a platinum group component and of a pyrolyzed rhenium carbonyl component. Substantially all of the platinum group component is, moreover, present in the composite in the elemental metallic state during the incorporation of the rhenium carbonyl component and the pyrolysis of the rhenium carbonyl component is performed after it has been reacted with the porous carrier material containing the platinum group component. Further, these components are preferably present in this composite in amounts, calculated on an elemental basis, sufficient to result in the composite containing about 0.01 to about 2 wt. % platinum group metal, and about 0.01 to about 5 wt. % rhenium derived from the rhenium carbonyl component, and this composite is preferably maintained in a substantially halogen-free state during use in the dehydrogenation method.

A second embodiment relates to the dehydrogenation method described in the first embodiment wherein the dehydrogenatable hydrocarbon is an aliphatic compound containing 2 to 30 carbon atoms per molecule.

A third embodiment comprehends a superactive nonacidic catalytic composite comprising a porous carrier material having uniformly dispersed therein catalytically effective and available amounts of a platinum group component, a pyrolyzed rhenium carbonyl component, and an alkali or alkaline earth component. These components are preferably present in amounts sufficient to result in the catalytic composite containing, on an elemental basis, about 0.01 to about 2 wt. % platinum group metal, about 0.1 to about 5 wt. % of the alkali metal or alkaline earth metal and about 0.01 to about 5 wt. % rhenium, derived from the rhenium carbonyl component. In addition, substantially all of the platinum group component is present in the elemental metallic state during incorporation of the rhenium carbonyl component, the pyrolysis of the rhenium carbonyl component occurs after combustion thereof with the porous carrier material containing the platinum group component and substantially all of the alkali or alkaline earth component is present in an oxidation state above that of the elemental metal.

Another embodiment pertains to a method for dehydrogenating a dehydrogenatable hydrocarbon which comprises contacting the hydrocarbon with the nonacidic catalytic composite described in the third embodiment at dehydrogenation conditions.

Other objects and embodiments of the present invention involve specific details regarding essential and preferred catalytic ingredients, preferred amounts of ingredients, suitable methods of multimetallic composite preparation, suitable dehydrogenatable hydrocarbons, operating conditions for use in the dehydrogenation process, and the like particulars. These are hereinafter given in the following detailed discussion of each of these facets of the present invention. It is to be understood that (1) the term "nonacidic" means that the catalyst produces less than 10% conversion of 1-butene to isobutylene when tested at dehydrogenation conditions and, preferably, less than 1%; (2) the expression "uniformly dispersed throughout a carrier material" is intended to mean that the amount of the subject component, expressed on a weight percent basis, is approximately the same in any reasonably divisible portion of the carrier material as it is in gross; and (3) the term "substantially halogen-free" means that the total amount of halogen present in the catalytic composite in any form is less than about 0.2 wt. %, calculated on an elemental basis.

Regarding the dehydrogenatable hydrocarbon that is subjected to the method of the present invention, it can, in general, be an organic compound having 2 to 30 carbon atoms per molecule and containing at least one pair of adjacent carbon atoms having hydrogen attached thereto. That is, it is intended to include within the scope of the present invention, the dehydrogenation of any organic compound capable of being dehydrogenated to produce products containing the same number of carbon atoms but fewer hydrogen atoms, and capable of being vaporized at the dehydrogenation temperatures used herein. More particularly, suitable dehydrogenatable hydrocarbons are: aliphatic hydrocarbons containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, and the like compounds; (2) naphthenes such as cyclopentane, cyclohexane, methylcyclopentane, ethylcyclopentane, n-propylcyclopentane, 1,3-dimethylcyclohexane, and the like compounds; and (3) alkylaromatics such as ethylbenzene, n-butylbenzene, 1,3,5-triethylbenzene, isopropylbenzene, isobutylbenzene, ethylnaphthalene, and the like compounds.

In a preferred embodiment, the dehydrogenatable hydrocarbon is a normal paraffin hydrocarbon having about 3 to 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biogradability. Likewise, n-alkanes having 10 to 18 carbon atoms per molecule can be dehydrogenated to the corresponding normal mono-olefin which, in turn, can be sulfonated or sulfated to make excellent detergents. Similarly, n-alkanes having 6 to 10 carbon atoms can be dehydrogenated to form the corresponding mono-olefin which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$ and the like mixtures. In an especially preferred embodiment, charge stock to present method is substantially pure propane.

The superactive multimetallic catalyst used in the present invention comprises a porous carrier material or support having combined therewith a uniform dispersion of catalytically effective amounts of a platinum group component, a pyrolyzed rhenium carbonyl component, and, in the preferred case, an alkali or alkaline earth component.

Considering first the porous carrier material utilized in the present invention, it is preferred that the material be a porous, adsorptive, high surface area support having a surface area of about 25 to about 500 $m^2/g$. The porous carrier material should be relatively refractory to the conditions utilized in the hydrocarbon dehydrogenation process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms (B.E.T.), the pore volume is about 0.1 to about 1 cc/g (B.E.T.) and the surface area is about 100 to about 500 $m^2/g$ (B.E.T.). In general, best results are typically obtained with a substantially halogen-free gamma-alumina carrier material which is used in the form of spherical particles having a relatively small diameter (i.e. typically about 1/16 inch), an apparent bulk density of about 0.2 to about 0.8 g/cc, a pore volume of about 0.3 to about 0.8 cc/g (B.E.T.), and a surface area of about 125 to about 250 m²/g (B.E.T.).

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere, and alumina spheres may be continuously manufactured by the well known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characterisics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. It is a good practice to subject the calcined particles to a high temperature treatment with steam in order to remove undesired acidic components such as residual chlorine and thereby prepare the preferred substantially halogen-free carrier material. This preparation procedure effects conversion of the alumina hydrogel to the corresponding crystalline gamma-alumina. See the teachings of U.S. Pat. No. 2,620,314 for additional details.

Another particularly preferred alumina carrier material is synthesized from a unique crystalline alumina powder which has been characterized in U.S. Pat. Nos. 3,852,190 and 4,012,313 as a by-product from a Ziegler higher alcohol synthesis reaction as described in Ziegler's U.S. Pat. No. 2,892,858. For purposes of simplification, the name "Ziegler alumina" is used herein to identify this material. It is presently available from the Conoco Chemical Division of Continental Oil Company under the trademark Catapal. This material is an extremely high purity alpha-alumina monohydrate (boehmite) which after calcination at a high temperature has been shown to yield a high purity gamma-alumina. It is commercially available in three forms: (1) Catapal SB—a spray dried powder having a typical surface area of 250 m²/g; (2) Catapal NG—a rotary kiln dried alumina having a typical surface area of 180 m²/g; and (3) Dispal M—a finely divided dispersable product having a typical surface area of about 185 m²/g. For purposes of the present invention, the preferred starting material is the spray dried powder, Catapal SB. Thia alpha-alumina monohydrate powder may be formed into a suitable catalyst material according to any of the techniques known to those skilled in the catalyst carrier material forming art. Spherical carrier material particles can be formed, for example, from this Ziegler alumina by: (1) converting the alpha-alumina monohydrate powder into an alumina sol by reaction with a suitable peptizing acid and water and thereafter dropping a mixture of the resulting sol and a gelling agent into an oil bath to form spherical particles of an alumina gel which are easily converted to a gamma-alumina carrier material by known methods; (2) forming an extrudate from the powder by established methods and thereafter rolling the extrudate particles on a spinning disc until spherical particles are formed which can then be dried and calcined to form the desired particles of spherical carrier material; and (3) wetting the powder with a suitable peptizing agent and thereafter rolling particles of the powder into spherical masses of the desired size in much the same way that children have been known to make parts of snowmen by rolling snowballs down hills covered with wet snow. This alumina powder can also be formed in any other desired shape or type of carrier material known to those skilled in the art such as rods, pills, pellets, tablets, granules, extrudates and the like forms by methods well known to the practitioners of the catalyst carrier material forming art. The preferred type of carrier material for the present invention is a cylindrical extrudate having a diameter of about 1/32" to about ⅛" (especially about 1/16") and a length to diameter (L/D) ratio of about 1:1 to about 5:1, with L/D ratio of about 2:1 being especially preferred. The especially preferred extrudate form of the carrier material is preferably prepared by mixing the alumina powder with water and a suitable peptizing agent such as nitric acid, acetic acid, aluminum nitrate and the like material until an extrudable dough is formed. The amount of water added to form the dough is typically sufficient to give a loss of ignition (LOI) at 500° C. of about 45 to 65 wt. %, with a value of about 55 wt. % being especially preferred. On the other hand, the acid addition rate is generally sufficient to provide about 2 to 7 wt. % of the volatile free alumina powder used in the mix, with a value of about 3 to 4% being especially preferred. The resulting dough is then extruded through a suitably sized die to form extrudate particles. It is to be noted that it is within the scope of the present invention to treat the resulting dough with an aqueous alkaline reagent such as an aqueous solution of ammonium hydroxide in accordance with the teachings of U.S. Pat. No. 3,661,805. This treatment may be performed either before or after extrusion, with the former being preferred. These particles are then dried at a temperature of about 500° to 800° F. for a period of about 0.1 to about 5 hours and thereafter calcined at a temperature of about 900° F. to about 1500° F. for a period of about 0.5 to about 5 hours to form the preferred extrudate particles of the Ziegler alumina carrier material. In addition, in some embodiments of the present invention the Ziegler alumina carrier material may contain minor proportions of other well known refractory inorganic oxides such as silica, titanium dioxide, zirconium dioxide, chromium oxide, beryllium oxide, vanadium oxide, cesium oxide, hafnium oxide, zinc oxide, iron oxide, cobalt oxide, magnesia, boria, thoria, and the like materials which can be blended into the extrudable dough prior to the extrusion of same. In the same manner crystalline zeolitic aluminosilicates such as naturally occurring or synthetically prepared mordenite and/or faujasite, either in the hydrogen form or in a form which has been treated with a multivalent cation, such as a rare earth, can be incorporated into this carrier material by blending finely divided particles of same into the extrudable dough prior to extrusion of same. A preferred carrier material of this type is a substantially halogen-free and substantially pure Ziegler alumina having an apparent bulk density (ABD) of about 0.4 to 1 g/cc (especially an ABD of about 0.5 to about 0.85 g/cc), a surface area (B.E.T.) of about 150 to about 280 m$^2$/g (preferably about 185 to about 235 m$^2$/g) and a pore volume (B.E.T.) of about 0.3 to about 0.8 cc/g.

A first essential ingredient of the subject catalyst is the platinum group component. That is, it is intended to cover the use of platinum, iridium, osmium, ruthenium, rhodium, palladium, or mixtures thereof as a first component of the superactive catalytic composite. It is an essential feature of the present invention that substantially all of this platinum group component is uniformly dispersed throughout the porous carrier material in the elemental metallic state prior to the incorporation of the rhenium carbonyl ingredient. Generally, the amount of this component present in the form of catalytic composites is small and typically will comprise about 0.01 to about 2 wt. % of final catalytic composite, calculated on an elemental basis. Excellent results are obtained when the catalyst contains about 0.05 to about 1 wt. % of platinum, iridium, rhodium or palladium metal. Particularly preferred mixtures of these platinum group metals preferred for use in the composite of the present invention are: (1) platinum and iridium and (2) platinum and rhodium.

This platinum group component may be incorporated in the porous carrier material in any suitable manner known to result in a relatively uniform distribution of this component in the carrier material such as coprecipitation or cogelation, ion-exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other water-soluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium cloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium, or palladium chloride compound, such as chloroplatinic, chloroiridic, or chloropalladic acid or rhodium trichloride hydrate, is ordinarily preferred. Nitric acid or the like acid is also generally added to the impregnation solution in order to further facilitate the uniform distribution of the metallic components throughout the carrier material. In addition, it is generally preferred to impregnate the carrier material after it has been calcined in order to minimize the risk of washing away the valuable platinum group component.

A highly preferred optional ingredient of the catalyst used in the present invention is the alkali or alkaline earth component. More specifically, this component is selected from the group consisting of the compounds of the alkali metals—cesium, rubidium, potassium, sodium, and lithium—and of the alkaline earth metals—calcium, strontium, barium, and magnesium. This component exists within the catalytic composite in an oxidation state above that of the elemental metal such as a relatively stable compound such as the oxide or hydroxide, or in combination with one or more of the other components of the composite, or in combination with the carrier material such as, for example, in the form of an alkali or alkaline earth metal aluminate. Since, as is explained hereinafter, the composite containing the alkali or alkaline earth component is always calcined or oxidized in an air atmosphere before use in the dehydrogenation of hydrocarbons, the most likely state this component exists in during use in the dehydrogenation reaction is the corresponding metallic oxide such as lithium oxide, potassium oxide, sodium oxide, and the like. Regardless of what precise form in which it exists in the composite, the amount of this component utilized is preferably selected to provide a nonacidic composite containing about 0.1 to about 5 wt. % of the alkali metal or alkaline earth metal, and, more preferably, about 0.25 to about 3.5 wt. %. Best results are obtained when this component is a compound of lithium or potassium. The function of this component is to neutralize any of the acidic material such as halogen which may have been used in the preparation of the present catalyst so that the final catalyst is nonacidic.

This alkali or alkaline earth component may be combined with the porous carrier material in any manner known to those skilled in the art to result in a relatively uniform dispersion of this component throughout the carrier material with consequential neutralization of any acidic sites which may be present therein. Typically good results are obtained when it is combined by impregnation, coprecipitation, ion-exchange, and the like procedures. The preferred procedure, however, involves impregnation of the carrier material either before, during or after it is calcined, or before, during, or after the other metallic ingredients are added to the carrier material. Best results are ordinarily obtained when this component is added to the carrier material simultaneously with or after the platinum group component and before the rhenium carbonyl component because the alkali metal or alkaline earth metal component acts to neutralize the acidic materials used in the preferred impregnation procedure for the platinum group component. In fact, it is preferred to add the platinum group and alkali or alkaline earth components to the carrier material, oxidize the resulting composite in a wet air stream at a high temperature (i.e. typically about 600° to 1000° F.), then treat the resulting oxidized composite with steam or a mixture of air and steam at a relatively high temperature of about 600° to about 1050° F. in order to remove at least a portion of any residual acidity and thereafter add the rhenium carbonyl component. Typically, the impregnation of the carrier material with this component is performed by contacting the carrier material with a solution of a suitable decomposable compound or salt of the desired alkali or alkaline earth metal. Hence, suitable compounds include the alkali or alkaline earth metal halides, nitrates, acetates, carbonates, phosphates, and the like compounds. For example, excellent results are obtained by impregnating the carrier material with an aqueous solution of chloroplatinic acid, lithium nitrate or potassium nitrate and nitric acid. Ordinarily, the amount of alkali or alkaline earth component is selected to produce a composite having an atomic ratio of alkali metal or alkaline earth metal to platinum group metal of about 5:1 to about 100:1 or more, with the preferred range being about 10:1 to about 75:1.

After the platinum group component and the optional alkali or alkaline earth component are combined with the porous carrier material, the resulting metals-containing carrier material will generally be dried at a temperature of about 200° F. to about 600° F. for a period of typically about 1 to about 24 hours or more and thereafter oxidized at a temperature of about 600° F. to about 1000° F. in an air or oxygen atmosphere for a period of about 0.5 to about 10 or more hours effective to convert substantially all of the platinum group and the alkali or alkaline earth components to the corresponding oxide forms. When acidic materials are used in incorporating these metallic components, best results are ordinarily achieved when the resulting oxidized composite is subjected to a high temperature treatment with steam or with a mixture of steam and a diluent gas such as air or nitrogen either during or after this oxidation step in order to remove as much as possible of the undesired acidic components such as halogen and thereby prepare a substantially halogen-free, metals-containing oxidized carrier material. It is to be noted that it is essential that conditions used in this acidic component stripping step be very carefully chosen to avoid any possibility of sintering or agglomerating the platinum group component.

A critical feature of the present invention involves subjecting the resulting oxidized, platinum group metal-containing, and typically alkali or alkaline earth metal-containing carrier material to a substantially water-free reduction step before the incorporation of the rhenium component by means of the rhenium carbonyl reagent. The importance of this reduction step comes from my observation that when an attempt is made to prepare the instant catalytic composite without first reducing the platinum group component, no significant improvement in the platinumrhenium catalyst system is obtained; put another way, it is my finding that it is essential for the platinum group component to be well dispersed in the porous carrier material in the elemental metallic state prior to incorporation of the rhenium component by the unique procedure of the present invention in order for synergistic interaction of the rhenium carbonyl with the dispersed platinum group metal to occur according to the theories that I have previously explained in my prior application Ser. No. 833,332. Accordingly, this reduction step is designed to reduce substantially all of the platinum group component to the elemental metallic state and to assure a relatively uniform and finely divided dispersion of this metallic component throughout the porous carrier material. Preferably, a substantially pure and dry hydrogen-containing stream (by the use of the word "dry" I mean that it contains less than 20 vol. ppm. water and preferably less than 5 vol. ppm. water) is used as the reducing agent in this step. The reducing agent is contacted with the oxidized, platinum group metal-containing carrier material at conditions including a reduction temperature of about 450° F. to about 1200° F. for a period of about 0.5 to about 10 or more hours selected to reduce substantially all of the platinum group component to the elemental metallic state. Once this condition of finely divided dispersed platinum group metal in the porous carrier material is achieved, it is important that environments and/or conditions that could disturb or change this condition be avoided; specifically, I much prefer to maintain the freshly reduced carrier material containing the platinum group metal under a blanket of inert gas to avoid any possibility of contamination of same either by water or by oxygen.

A second essential ingredient of the present superactive catalytic composite is a rhenium component which I have chosen to characterize as a pyrolyzed rhenium carbonyl component in order to emphasize that the rhenium moiety of interest in my invention is the rhenium produced by decomposing a rhenium carbonyl in the presence of a finely divided dispersion of a platinum group metal and in the absence of materials such as oxygen or water which could interfere with the desired interaction of the rhenium carbonyl component with the platinum group metal component. In view of the fact that all of the rhenium contained in a rhenium carbonyl compound is present in the elemental metallic state, an essential requirement of my invention is that the resulting reaction product of the rhenium carbonyl compound or complex with the platinum group metal-loaded carrier material is not subjected to conditions which could in any way interfere with the maintenance of the rhenium moiety in the elemental metallic state; consequently, avoidance of any conditions which would tend to cause the oxidation of any portion of the rhenium ingredient or of the platinum group ingredient is a requirement for full realization of the synergistic interaction enabled by the present invention. This rhenium component may be utilized in the resulting composite in any amount that is catalytically effective with the preferred amount typically corresponding to about 0.01 to about 5 wt. % thereof, calculated on an elemental rhenium basis. Best results are ordinarily obtained with about 0.05 to about 1 wt. % rhenium. The traditional rule for rhenium-platinum catalyst system is that best results are achieved when the amount of the rhenium component is set as a function of the amount of the platinum group component also hold for my composition; specifically, I find that best results with a rhenium to platinum group metal atomic ratio of about 0.1:1 to about 10:1, with an especially useful range comprising about 0.2:1 to about 5:1 and with superior results achieved at an atomic ratio of rhenium to platinum group metal of about 1:1.

The rhenium carbonyl ingredient may be reacted with the reduced platinum group metal-containing porous carrier material in any suitable manner known to those skilled in the catalyst formulation art which results in relatively good contact between the rhenium carbonyl complex and the platinum group component contained in the porous carrier material. One acceptable procedure for incorporating the rhenium carbonyl compound into the composite involves sublimating the rhenium carbonyl complex under conditions which enables it to pass into the vapor phase without being decomposed and thereafter contacting the resulting rhenium carbonyl sublimate with the platinum group metal-containing porous carrier material under conditions designed to achieve intimate contact of the carbonyl reagent with the platinum group metal dispersed on the carrier material. Typically, this procedure is performed under vacuum at a temperature of about 70° to about 250° F. for a period of time sufficient to react the desired amount of rhenium carbonyl complex with the carrier material. In some cases an inert carrier gas such as nitrogen can be admixed with the rhenium carbonyl sublimate in order to facilitate the intimate contacting of same with the platinum-loaded porous carrier material. A particularly preferred way of accomplishing this rhenium carbonyl reaction step is an impregnation procedure wherein the platinum-loaded porous carrier material is impregnated with a suitable solution containing the desired quantity of the rhenium carbonyl complex. For purposes of the present invention, organic solutions are preferred, although any suitable solution may be utilized as long as it does not interact with the rhenium carbonyl complex and cause decomposition of same. Obviously, the organic solution should be anhydrous in order to avoid detrimental interaction of water with the rhenium carbonyl complex. Suitable solvents are any of the commonly available organic solvents such as one of the available ethers, alcohols, ketones, aldehydes, paraffins, naphthenes and aromatic hydrocarbons, for example, acetone, acetyl acetone, benzaldehyde, pentane, hexane, carbon tetrachloride, methyl isopropyl ketone, benzene, n-butylether, diethyl ether, ethylene glycol, methyl isobutyl ketone, diisobutyl ketone and the like organic solvents. Best results are ordinarly obtained when the solvent is acetone; consequently, the preferred impregnation solution is rhenium carbonyl complex dissolved in anhydrous acetone. The rhenium carbonyl complex suitable for use in the present invention may be either the pure rhenium carbonyl itself or a substituted rhenium carbonyl such as the rhenium carbonyl halides including the chlorides, bromides, and iodides and the like substituted rhenium carbonyl complexes. After impregnation of the carrier material with the rhenium carbonyl component, it is important that the solvent be removed or evaporated from the catalyst prior to decomposition of the rhenium carbonyl component by means of the hereinafter described pyrolysis step. The reason for removal of the solvent is that I believe that the presence of organic materials such as hydrocarbons or derivatives of hydrocarbons during the rhenium carbonyl pyrolysis step is highly detrimental to the synergistic interaction associated with the present invention. This solvent is removed by subjecting the rhenium carbonyl impregnated carrier material to a temperature of about 100° F. to about 250° F. in the presence of an inert gas or under a vacuum condition until substantially no further solvent is observed to come off the impregnated material. In the preferred case where acetone is used as the impregnation solvent, this drying of the impregnated carrier material typically takes about one half hour at a temperature of about 225° F. under moderate vacuum conditions.

After the rhenium carbonyl component is incorporated into the platinum-loaded porous carrier material, the resulting composite is, pursuant to the present invention, subjected to pyrolysis conditions designed to decompose substantially all of the rhenium carbonyl material, without oxidizing either the platinum group or the decomposed rhenium carbonyl component. This step is preferably conducted in an atmosphere which is substantially inert to the rhenium carbonyl complex such as in a nitrogen or noble gas-containing atmosphere. Preferably, this pyrolysis step takes place in the presence of a substantially pure and dry hydrogen stream. It is of course within the scope of the present invention to conduct the pyrolysis step under vacuum conditions. It is much preferred to conduct this step in the substantial absence of free oxygen and substances that could yield free oxygen under the conditions selected. Likewise, it is clear that best results are obtained when this step is performed in the total absence of water and of hydrocarbons and other organic materials. I have obtained best results in pyrolyzing rhenium carbonyl while using an anhydrous hydrogen stream at pyrolysis conditions including a temperature of about 300° F. to about 900° F. or more, preferably about 400° F. to about 750° F., a gas hourly space velocity of about 250 to about 1500 hr.$^{-1}$ for a period of about 0.5 to about 5 or more hours until no further evolution of carbon monoxide is noted. After the rhenium carbonyl component has been pyrolyzed, it is a much preferred practice to maintain the resulting catalytic composite in an inert environment (i.e. a nitrogen or the like inert gas blanket) until the catalyst is loaded into a reaction zone for use in the dehydrogenation of hydrocarbons.

The resulting pyrolyzed catalytic composite may, in some cases, be beneficially subjected to a presulfiding step designed to incorporate in the catalytic composite from about 0.01 to about 1 wt. % sulfur calculated on an elemental basis. Preferably, this presulfiding treatment takes place in the presence of hydrogen and a suitable decomposable sulfur-containing compound such as hydrogen sulfide, lower molecular weight mercaptans, organic sulfides, etc. Typically, this procedure comprises treating the pyrolyzed catalyst with a sulfiding gas such as a mixture of hydrogen and hydrogen sulfide containing 1 to about 10 moles of hydrogen per mole of hydrogen sulfide at conditions sufficient to effect the desired incorporation of sulfur, generally including a temperature ranging from about 50° F. up to about 1000° F. It is generally a preferred practice to perform this presulfiding step under substantially water-free and oxygen-free conditions. It is within the scope of the present invention to maintain or achieve the sulfided state of the present catalyst during use in the dehydrogenation of hydrocarbons by continuously or periodically adding a decomposable sulfur-containing compound, selected from the above-mentioned hereinbefore, to the reactor containing the superactive catalyst in an amount sufficient to provide about 1 to 500 wt. ppm., preferably about 1 to about 20 wt. ppm. of sulfur, based on hydrocarbon charge. According to another mode of operation, this sulfiding step may be accomplished during the pyrolysis step by utilizing a rhenium carbonyl reagent which has a sulfur-containing ligand or by adding H$_2$S to the hydrogen stream which is preferably used therein.

According to the method of the present invention, the dehydrogenatable hydrocarbon is contacted with the superactive multimetallic catalytic composite described above in a dehydrogenation zone maintained at dehydrogenation conditions. This contacting may be accomplished by using the catalyst in a fixed bed system, a moving bed system, a fluidized bed system, or in a batch type operation; however, in view of the danger of attrition losses of the valuable catalyst and of well-known operational advantages, it is preferred to use a fixed bed system. In this system, the hydrocarbon feed stream is preheated by any suitable heating means to the desired reaction temperature and then passed into a dehydrogenation zone containing a fixed bed of the catalyst previously characterized. It is, of course, understood that the dehydrogenation zone may be one or more separate reactors with suitable heating means therebetween to insure that the desired conversion temperature is maintained at the entrance to each reactor. It is also to be noted that the reactants may be contacted with the catalyst bed in either upward, downward, or radial flow fashion with the latter being preferred. In addition, it is to be noted that the reactants may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized, either individually or in admixture with hydrogen or each other, such as steam, methane, ethane, carbon dioxide, and the like diluents. Hydrogen is preferred because it serves the dual-function of not only lowering the partial pressure of the dehydrogenatable hydrocarbon, but also of suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycled hydrogen obtained from the effluent stream from this zone after a suitable hydrogen separation step. As explained in my prior application Ser. No. 833,332, a highly preferred mode of operation of the instant dehydrogenation method is in a substantially water-free environment; however, when utilizing hydrogen in the instant method, improved selectivity results are obtained under certain limited circumstances, if water or a water-producing substance (such as an alcohol), ketone, ether, aldehyde, or the like oxygen-containing decomposable organic compound) is added to the dehydrogenation zone in an amount calculated on the basis of equivalent water, corresponding to about 1 to about 5,000 wt. ppm. of the hydrocarbon charge stock, with about 1 to 1,000 wt. ppm. of water giving best results. This water addition feature may be used on a continuous or intermittent basis to regulate the activity and selectivity of the instant catalyst.

Regarding the conditions utilized in the method of the present invention, these are generally selected from the dehydrogenation conditions well known to those skilled in the art for the particular dehydrogenatable hydrocarbon which is charged to the process. More specifically, suitable conversion temperatures are selected from the range of about 700° to about 1300° F. with a value being selected from the lower portion of this range for the more easily dehydrogenated hydrocarbons such as the long chain normal paraffins and from the higher portion of this range for the more difficulty dehydrogenated hydrocarbons such as propane, butane, and the like hydrocarbons. For example, for the dehydrogenation of $C_6$ to $C_{30}$ normal paraffins, best results are ordinarily obtained at a temperature of about 800° to about 950° F.; on the other hand, for the dehydrogenation of propane, best results are usually achieved at a temperature of about 1150° F. to 1250° F. The pressure utilized is ordinary selected at a value which is as low as possible consistent with the maintenance of catalyst stability and is usually about 0.1 to about 10 atmospheres with best results ordinarily obtained in the range of about 0.5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long-chain normal paraffins typically obtained at a relatively high space velocity of about 20 to 35 hr.$^{-1}$ and for the more refractory paraffins at a space velocity of about 3 to about 10 hr.$^{-1}$.

Regardless of the details concerning the operations of the dehydrogenation step, an effluent stream will be withdrawn therefrom. This effluent will usually contain unconverted dehydrogenatable hydrocarbons, hydrogen, and products of the dehydrogenation reaction. This stream is typically cooled and passed to a hydrogen-separating zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery operation can be accomplished in any suitable manner known to the art such as by-passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbon, or by a suitable fractionation scheme where feasible. In the case where the dehydrogenated hydrocarbon is a mono-olefin, suitable adsorbents having this capability are activated silica gel, activated carbon, activated alumina, various types of specially prepared zeolitic crystalline alumino-silicates, molecular sieves, and the like adsorbents. In another typical case, the dehydrogenated hydrocarbons can be separated from the unconverted dehydrogentable hydrocarbons by utilizing the inherent capability of the dehydrogenated hydrocarbons to easily enter into several well-known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the hydrogen phase present in the hydrogen-separating zone will be withdrawn therefrom, a portion of it vented from the system in order to remove the net hydrogen make, and the remaining portion is typically recycled through suitable compressing means to the dehydrogenation step in order to provide diluent hydrogen therefor.

In a preferred embodiment of the present invention wherein long chain normal paraffin hydrocarbons are dehydrogenated to the corresponding normal monoolefins, a preferred mode of operation of this hydrocarbon recovery step involves an alkylation reaction. In this mode, the hydrocarbon-rich liquid phase withdrawn from the hydrogen-separating zone is combined with a stream containing an alkylatable aromatic and the resulting mixture passed to an alkylation zone containing a suitable highly acid catalyst such as an anhydrous solution of hydrogen fluoride. In the alkylation zone the mono-olefins react with alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation step of the present invention.

The following working examples are introduced to illustrate further the dehydrogenation method and the superactive multimetallic catalytic composite of the present invention. These examples of specific embodiments of the present invention are intended to be illustrative rather than restrictive.

These examples are all performed in a laboratory scale dehydrogenation plant comprising a reactor, a hydrogen separating zone, heating means, cooling means, pumping means, compressing means, and the like conventional equipment. In this plant, the feed stream containing the dehydrogenable hydrocarbon is combined with a hydrogen-containing, substantially water-free, recycle gas stream and the resultant mixture heated to the desired conversion temperature, which refers herein to the temperature maintained at the inlet to the reactor. The heated mixture is then passed into contact with the instant superactive multimetallic catalyst which is maintained as fixed bed of catalyst particles in the reactor. The pressures reported herein are recorded at the outlet from the reactor. An effluent stream is withdrawn from the reactor, cooled, and passed into the hydrogen-separating zone wherein a hydrogen-containing gas phase separates from a hydrocarbon-rich liquid phase containing dehydrogenated hydrocarbons, unconverted dehydrogenatable hydrocarbons, and a minor amount of side products of the dehydrogenation reaction. A portion of the hydrogen-containing gas phase is recovered as excess recycle gas with the remaining portion being continuously recycled, after water addition as needed, through suitable compressing means to the heating zone as described above. The hydrocarbon-rich liquid phase from the separating zone is withdrawn therefrom and subjected to analysis to determine conversion and selectivity for the desired dehydrogenated hydrocarbon as will be indicated in the Examples. Conversion numbers of the dehydrogenable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the catalysts utilized in these examples are prepared according to the following preferred method with suitable modification in stoichiometry to achieve the compositions reported im each example. First, an alumina carrier material comprising 1/16 inch spheres having an apparent bulk density of about 0.3 g/cc is prepared by: forming an alumina hydroxyl chloride sol by dissolving substantially pure aluminum pellets in a hydrochloric acid solution, adding hexamethylenetetramine to the resulting alumina sol, gelling the resulting solution by droppin it into an oil bath to form spherical particles of an alumina hydrogel, aging, and washing the resulting particles with an ammoniacal solution and finally drying, calcining and steaming the aged and washed particles to form spherical particles of a substantially halogen-free gamma-alumina containing substantially less than 0.1 wt. % combined chloride. Additional details as to this method of preparing this alumina carrier material are given in the teachings of U.S. Pat. No. 2,620,314.

An aqueous impregnation solution containing chloroplatinic acid, nitric acid and (when an alkali or alkaline earth component is used) either lithium nitrate or potassium nitrate is then prepared. The alumina carrier material is thereafter admixed with the impregnation solution. The amounts of the metallic reagents contained in this impregnation solution are calculated to result in a final composite containing the hereinafter specified amounts of the metallic components. In order to insure uniform dispersion of the platinum component throughout the carrier material, the amount of nitric acid used in this impregnation solution is about 5 wt. % of the alumina particles. This impregnation step is performed by adding the carrier material particles to the impregnation mixture with constant agitation. In addition, the volume of the solution is approximately the same as the bulk volume of the alumina carrier material particles so that all of the particles are immersed in the impregnation solution. The impregnation mixture is maintained in contact with the carrier material particles for a period of about ½ to about 3 hours at a temperature of about 70° F. Thereafter, the temperature of the impregnation mixture is raised to about 225° F. and the excess solution is evaporated in a period of about 1 hour. The resulting dried impregnated particles are then subjected to an oxidation treatment in a dry air stream at a temperature of about 975° F. and a GHSV of about 500 hr.$^{-1}$ for about ½ hour. This oxidation step is designed to convert substantially all of the metallic ingredients to the corresponding oxide forms. The resulting oxidized spheres are subsequently contacted in a steam stripping step with an air stream containing about 1 to about 30% steam at a temperature of about 800° to about 1000° F. for an additional period of about 1 to about 5 hours in order to reduce any residual combined chloride to a value less than 0.5 wt. % and most preferably less than 0.2 wt %. The oxidized and steam-stripped spheres are thereafter subjected to a second oxidation step with a dry air stream at 975° F. and a GHSV of 500 hr.$^{-1}$ for an additional period of about ½ hour.

The resulting oxidized, steam-stripped carrier material particles are then subjected to a dry reduction treatment designed to reduce substantially all of the platinum component to the elemental state and to maintain a uniform dispersion of this component in the carrier material. This reduction step is accomplished by contacting the particles with a hydrocarbon-free, dry hydrogen stream containing less than 5 vol. ppm. $H_2O$ at a temperature of about 1050° F., a pressure slightly above atmospheric, a flow rate of hydrogen through the particles corresponding to a GHSV of about 40 hr.$^{-1}$ and for a period of about one hour.

Rhenium carbonyl complex, $Re_2(CO)_{10}$, is thereafter dissolved in an anhydrous acetone solvent in order to prepare the rhenium carbonyl solution which was used as the vehicle for reacting rhenium carbonyl with the carrier material containing the uniformly dispersed platinum metal. The amount of the complex used is selected to result in a finished catalyst containing the hereinafter specified amount of carbonyl-derived rhenium metal. The resulting rhenium carbonyl solution is then contacted under appropriate impregnation conditions with the reduced, platinum-containing alumina carrier material resulting from the previously described reduction step. The impregnation conditions utilized are: a contact time of about one half to about three hours, a temperature of about 70° F. and a pressure of about atmospheric. It is important to note that this impregnation step is conducted under a nitrogen blanket so that oxygen is excluded from the environment and also this step was performed under anhydrous conditions. Thereafter, the acetone solvent is removed under flowing nitrogen at a temperature of about 175° F. for a period of about one hour. The resulting dry rhenium carbonyl impregnated particles are then subjected to a pyrolysis step designed to decompose the rhenium carbonyl component. This step involves subjecting the carbonyl impregnated particles to a flowing hydrogen stream at a first temperature of about 230° F. for about one half hour at a GHSV of about 600 hr.$^{-1}$ and at atmospheric pressure. Thereafter, in the second portion of the pyrolysis step, the temperature of the impregnated particles is raised to about 575° F. for an additional interval of about one hour until the evolution of CO was no longer evident. The resulting catalyst is then maintained under a nitrogen blanket until it was loaded into the reactor in the subsequently described reforming test.

EXAMPLE I

The reactor is loaded with 100 cc of a catalyst containing, on an elemental basis, 0.375 wt. % platinum, 0.375 wt. % rhenium, and less than 0.15 wt. % chloride. This corresponds to an atomic ratio of rhenium to platinum of 1.05:1. The feed stream utilized is commercial grade isobutane containing 99.7 wt. % isobutane and 0.3 wt. % normal butane. The feed stream is contacted with the catalyst at a temperature of 975° F., a pressure of 10 psig., a liquid hourly space velocity of 4.0 hr.$^{-1}$, and a recycle gas to hydrocarbon mole ratio of 3:1. The dehydrogenation plant is lined-out at these conditions and a 20 hour test period commenced. The hydrocarbon product stream from the plant is continuously analyzed by GLC (gas liquid chromatography) and a high conversion of isobutane is observed with a high selectivity for isobutylene.

EXAMPLE II

The catalyst contains, on an elemental basis, 0.375 wt. % platinum, 0.5 wt. % rhenium, 0.6 wt. % lithium, and less than 0.15 wt. % combined chloride. These amounts correspond to the following atomic ratios: Re/pt of 1.4:1 and Li/Pt of 45:1. The feed stream is commercial grade normal dodecane. The dehydrogenation reactor is operated at a temperature of 850° F., a pressure of 10 psig., a liquid hourly space velocity of 32 hr.$^{-1}$, and a recycle gas to hydrocarbon mole ratio of 5:1. After a line-out period, a 20 hour test period is performed during which the average conversion of the normal dodecane is maintained at a high level with a selectivity for normal dodecane of about 90%.

EXAMPLE III

The catalyst is the same as utilized in Example II. The feed stream is normal tetradecane. The conditions utilized are a temperature of 830° F., a pressure of 20 psig., a liquid hourly space velocity of 32 hr.$^{-1}$, and a recycle gas to hydrocarbon mole ratio of 4:1. After a line-out period, a 20 hour test shows an average conversion of about 12%, and a selectivity for normal tetradecane of about 90%.

EXAMPLE IV

The catalyst contains, on an elemental basis, 0.2 wt. % platinum, 0.2 wt. % rhenium, and 0.4 wt. % lithium, with combined chloride being less than 0.2 wt. %. The pertinent atomic ratios are: Re/Pt of 1.05:1 and Li/Pt of 56:1. The feed stream is substantially pure cyclohexane. The conditions utilized are a temperature of 900° F., a pressure of 100 psig., a liquid hourly space velocity of 3.0 hr.$^{-1}$, and a recycle gas to hydrocarbon mole ratio of 4:1. After a line-out period, a 20 hour test is performed with almost quantitative conversion of cyclohexane to benzene and hydrogen.

EXAMPLE V

The catalyst is the same as in Example IV. The feed stream is commercial grade ethylbenzene. The conditions utilized are a pressure of 15 psig., a liquid hourly space velocity of 32 hr.$^{-1}$, a temperature of 1010° F., and a recycle gas to hydrocarbon mole ratio of 3:1. During a 20 hour test period, 85% or more of equilibrium conversion of the ethylbenzene is observed. The selectivity for styrene is about 90%.

EXAMPLE VI

The catalyst contains, on an elemental basis, about 0.75 wt. % platinum, about 0.8 wt. % rhenium, about 0.6 wt. % lithium and less than 0.2 wt. % chlorine. The relevant atomic ratios are: Re/Pt of 1.12:1 and Li/Pt of 22.6:1. The charge stock is substantially pure propane. The conditions utilized are: an inlet reaction temperature of 1150° F., a pressure of 10 psig., a hydrogen to propane mole ratio of 2:1 and a liquid hourly space velocity of about 5 hr.$^{-1}$. Results are: a conversion of propane of about 35% at a selectivity for propylene of about 85%.

It is intended to cover by the following claims all changes and modifications of above disclosure of the present invention which would be self-evident to a man of ordinary skill in the catalyst-formulation art or in the hydrocarbon dehydrogenation art.

I claim as my invention:

1. A nonacidic catalytic composite comprising a catalytically effective amount of the pyrolyzed reaction product of a rhenium carbonyl component, wherein said rhenium carbonyl component is pyrolyzed in the presence of a reducing agent at a temperature of from about 300° F. to about 900° F., with a porous carrier material containing a uniform dispersion of a platinum group component maintained in the elemental metallic state and an alkali or alkaline earth component.

2. A nonacidic catalytic composite as defined in claim 1 wherein the composite contains the components in amounts, calculated on an elemental basis, corresponding to about 0.01 to about 2 wt. % platinum group metal, about 0.01 to about 5 wt. % rhenium and about 0.1 to about 5 wt. % alkali or alkaline earth metal.

3. A nonacidic catalytic composite as defined in claim 1 wherein the porous carrier material is a refractory inorganic oxide.

4. A nonacidic catalytic composite as defined in claim 3 wherein the refractory inorganic oxide is alumina.

5. A nonacidic catalytic composite as defined in claim 1 wherein the platinum group component is platinum.

6. A nonacidic catalytic composite as defined in claim 1 wherein the platinum group component is palladium.

7. A nonacidic catalytic composite as defined in claim 1 wherein the platinum group component is rhodium.

8. A nonacidic catalytic composite as defined in claim 1 wherein the platinum group component is iridium.

9. A nonacidic catalytic composite as defined in claim 1 wherein the alkali is potassium.

10. A nonacidic catalytic composite as defined in claim 1 Wherein the alkali is lithium.

11. A nonacidic catalytic composite as defined in claim 1 wherein the catalytic composite is in a substantially halogen-free state.

12. A nonacidic catalytic composite as defined in claim 1 wherein the composite contains, on an elemental basis, about 0.05 to about 1 wt. % platinum group metal, about 0.05 to about 1 wt. % rhenium and about 0.25 to about 3.5 wt. % alkali metal or alkaline earth metal.

* * * * *